(12) United States Patent
Kolattukudy et al.

(10) Patent No.: US 8,999,314 B2
(45) Date of Patent: Apr. 7, 2015

(54) MCPIP AS WOUND THERAPY

(71) Applicants: Pappachan E. Kolattukudy, Titusville, FL (US); Jianli Niu, Orlando, FL (US)

(72) Inventors: Pappachan E. Kolattukudy, Titusville, FL (US); Jianli Niu, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 14/257,334

(22) Filed: Apr. 21, 2014

(65) Prior Publication Data

US 2014/0341877 A1    Nov. 20, 2014

Related U.S. Application Data

(63) Continuation of application No. 13/804,275, filed on Mar. 14, 2013, now Pat. No. 8,703,703, and a continuation-in-part of application No. 12/539,907, filed on Aug. 12, 2009, and a continuation of application No. 11/643,057, filed on Dec. 20, 2006, now abandoned.

(51) Int. Cl.
| | | |
|---|---|---|
| *A61K 31/74* | (2006.01) |
| *A61K 38/46* | (2006.01) |
| *C07K 14/52* | (2006.01) |
| *C07K 14/47* | (2006.01) |
| *C12N 9/22* | (2006.01) |
| *A61K 48/00* | (2006.01) |
| *A61L 15/44* | (2006.01) |
| *A61K 9/00* | (2006.01) |
| *A61K 9/06* | (2006.01) |
| *A61F 13/02* | (2006.01) |
| *A61L 15/38* | (2006.01) |
| *A61K 38/00* | (2006.01) |
| *C12N 15/113* | (2010.01) |

(52) U.S. Cl.
CPC ............. *A61K 38/465* (2013.01); *C07K 14/523* (2013.01); *C07K 14/4705* (2013.01); *C12N 9/22* (2013.01); *A61K 48/005* (2013.01); *A61L 15/44* (2013.01); *A61K 9/0014* (2013.01); *A61K 9/0019* (2013.01); *A61K 9/06* (2013.01); *A61F 13/02* (2013.01); *A61L 15/38* (2013.01); *A61K 38/00* (2013.01); *A01K 2217/075* (2013.01); *A01K 2227/105* (2013.01); *A01K 2267/03* (2013.01); *C12N 15/1136* (2013.01); *C12N 2310/14* (2013.01); *A61L 2300/252* (2013.01); *A61L 2300/412* (2013.01)

(58) Field of Classification Search
USPC ...................................................... 424/78.06
See application file for complete search history.

(56) References Cited

U.S. PATENT DOCUMENTS

2004/0053396 A1 *  3/2004  Jackson et al. ............. 435/252.3

OTHER PUBLICATIONS

Kolattukudy et al., GenEmbl Database, Accession No. AY920403, Apr. 2005.*

* cited by examiner

*Primary Examiner* — Maryam Monshipouri
(74) *Attorney, Agent, or Firm* — Timothy H. Van Dyke; Beusse, Wolter, Sanks & Maire, P.A.

(57) ABSTRACT

Disclosed herein are methods and compositions of treating a subject suffering from a wound. In exemplary examples, the method involves elevating MCPIP levels in a subject in need. Elevating MCPIP levels may involve direct administration (e.g. delivery of protein) or indirect administration (e.g. delivery vehicle capable of increasing expression of MCPIP).

7 Claims, 4 Drawing Sheets

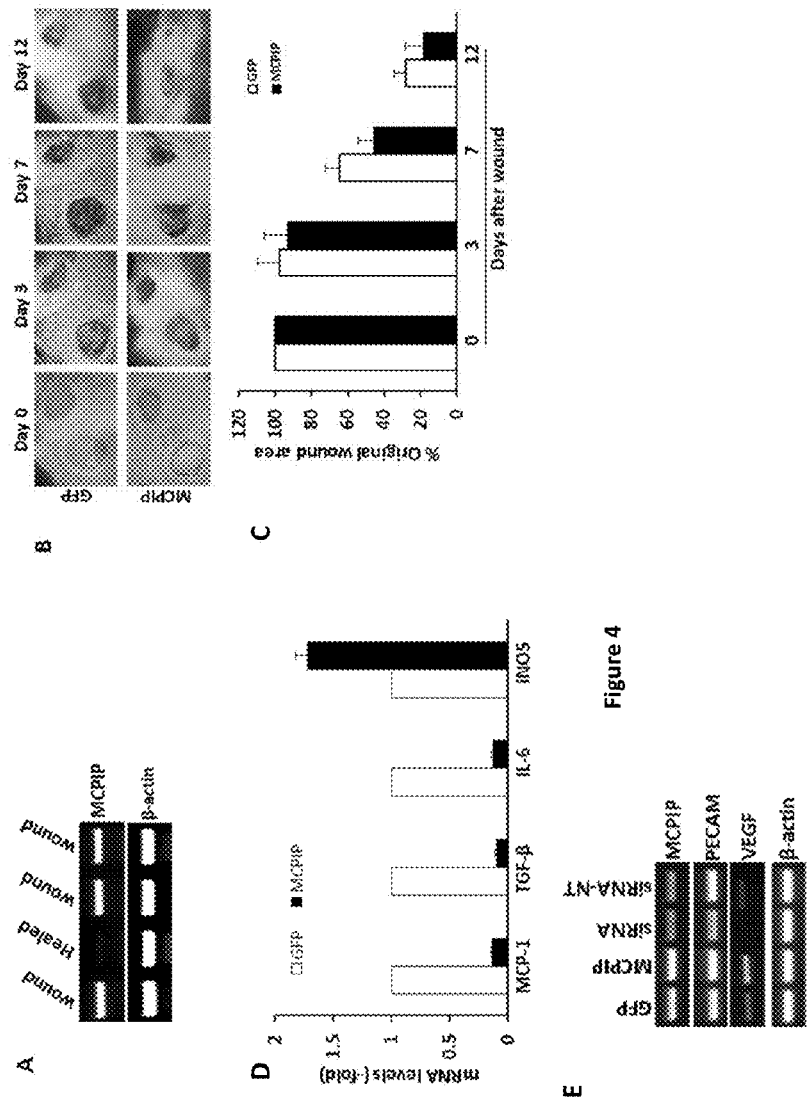

MCPIP AS WOUND THERAPY

RELATED APPLICATIONS

This application is a continuation of U.S. Ser. No. 13/804,275 filed Mar. 14, 2013, now issued as U.S. Pat. No. 8,703,703, which is a continuation-in-part of U.S. Ser. No. 12/539,907 filed Aug. 12, 2009, now abandoned, which is a continuation of U.S. Ser. No. 11/643,057 filed Dec. 20, 2006, now abandoned, which are incorporated herein in their entirety by reference.

BACKGROUND

Generally, when the skin of an individual is torn, cut or punctured (wounded), the body naturally reacts to regenerate dermal and epidermal tissue to close the wound. The wound regeneration process typically includes a set of complex biochemical events that take place in a closely orchestrated cascade to repair the damage. These events overlap in time, but may be categorized into different phases, namely the inflammatory, proliferative, and remodeling phases.

In the inflammatory phase, bacteria and debris are phagocytized and removed, and factors are released that cause the migration and division of cells involved in the proliferative phase. In the proliferative phase, the principal steps include angiogenesis, fibroplasias, granulation tissue formation, epithelialization, and wound contraction. Angiogeneis involves the development of new capillary blood vessels for the wound area to provide oxygen and nutrients to the healing tissue. In fibroplasia and granulation tissue formation, fibroblasts grow and form a new, provisional extracellular matrix (ECM) by excreting collagen and fibronectin. In epithelialization, epithelial cells crawl across the wound bed to cover the bed. In contraction, the wound is made smaller by the action of myofibroblasts, which establish a grip on the wound edges and contract themselves using a mechanism similar to that in smooth muscle cells. When the cells' roles are close to complete, unneeded cells undergo apoptosis.

It is known that a number of disease states hinder the normal wound healing process. For example, individuals with diabetes often experience problems with what are termed "diabetic foot ulcers." Diabetic foot ulcers are sores or wounds, typically, on the feet that typically occur in individuals having diabetes. Oftentimes, these diabetic ulcers occur as a direct or indirect result of nerve damage in the feet of the individual as the prolonged high blood sugar levels associated with diabetes is linked with damage to the nerves in the feet. Such nerve damage in the feet, referred to as peripheral neuropathy, can cause loss of sensation as well as cause deformities of the feet. Due to the loss of sensation, individuals with peripheral neuropathy may hurt their feet by repetitive minor trauma (e.g., by prolonged walking) or a single major trauma (e.g., by scraping skin, stepping on objects, immersing feet in hot water, cutting toenails inappropriately, or wearing ill-fitting shoes), but nevertheless may not notice such injuries. A further complication of diabetes is a reduction in blood flow to the feet due to the arterial blockage or other causes, thereby severely inhibiting the body's ability to adequately provide complete the proliferative stage of wound regeneration/healing described above. As a result, once the skin of the foot is torn, cut, or punctured, the wound healing process (e.g., the proliferative phase) may be inordinately slow in repairing the wound. Further, once a serious wound develops, the risk of infection is high as the individual's body is simply unable to heal the wound. Even further, once an infection starts, the infection may be very difficult to reverse, and amputation of the affected limb is common.

BRIEF DESCRIPTION OF THE DRAWINGS

FIG. 4. Expression of MCPIP enhanced wound healing in diabetic mice. (A) Induction of MCPIP was found in the wound skin but not in the healed skin. (B) Wound sites were photographed at the indicated time. Day 0 pictures were taken immediately after the wound. (C) Changes in percentage of wound area at each time point compared with the original wound area. (D) Expression of cytokines in wound skins at day 12 after wound. (F) Expression of PECAM and VEGF in wound skins at day 12 was examined by RT-PCR.

DETAILED DESCRIPTION

Figure 1:
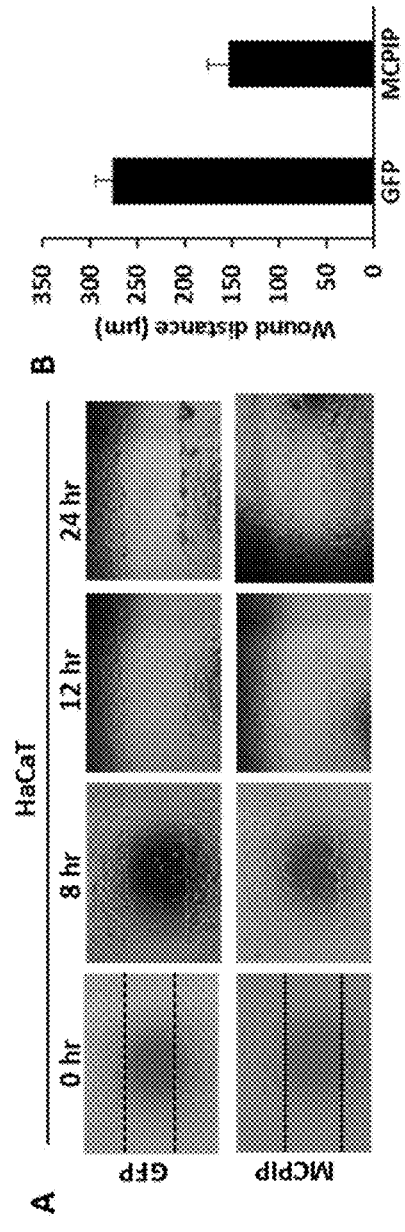
FIG. 1. Expression of MCPIP on scratch-induced wound healing in HaCaT cells. (A) Cells were cultured to confluence and transfected with GFP or MCPIP vectors for 48 hrs and wounded by scratching. Cells were then incubated for the indicated hours and photographed. (B) Quantification of scratch-induced wound healing during 24 hrs after scratching.

The inventors have previously identified the novel transcription factor designated as MCPIP (MCP-1-induced protein). MCPIP was initially isolated from human monocytes after stimulation with MCP-1. The nucleotide (SEQ ID NO: 1) and amino acid (SEQ ID NO: 2) sequences of isolated human MCPIP were deposited with GenBank under accession number AY920403 and the nucleotide (SEQ ID NO: 3) and amino acid (SEQ ID NO: 4) sequences of isolated mouse MCPIP were deposited with GenBank under accession number AY920404. The inventors have continued to study the biological relevance of these genes/proteins, and to develop new therapies based on this research. The invention is based on the inventors discovery that maintaining or elevating MCPIP levels can accelerate wound healing in a subject.

According to one embodiment, the invention pertains to a method of treating wounds. MCPIP may be elevated by direct administration of a composition. The composition may comprise a therapeutically effective amount of the MCPIP protein. The MCPIP protein composition may comprise a pharmaceutically acceptable excipient. Alternatively, MCPIP may be elevated by administering a composition comprising a delivery vehicle that results in the in vivo expression of MCPIP. In yet another embodiment, MCPIP is elevated by inducing expression of the endogenous gene.

As used herein, the use of the word "a" or "an" when used in conjunction with the term "comprising" in the claims and/or the specification may mean "one," but it is also consistent with the meaning of "one or more," "at least one," and "one or more than one."

The term "wound" as used herein refers to any break in the epithelium resulting from a cut, abrasion, adhesion, surgical incision, thermal, chemical, or friction burn, ulcer, or the like, as a result of an accident, incident, surgical procedure, or the like. Wound can be further defined as acute and/or chronic. Compositions of the present invention have been found to be particularly useful in the treatment of diabetic ulcers, which are a type of wound as defined herein.

The term "pharmaceutical composition" as used herein refers to a wound composition as described herein that this dispersed in a pharmaceutically acceptable carrier.

The term "subject" as used herein refers to any human or nonhuman mammalian animal to which a wound composition is administered according to the methods described herein. In a specific embodiment, the compositions and methods of the present invention are employed to treat a human subject.

The term "effective amount" or "therapeutically effective amount" as used herein refer to an amount effective, at dosages and for periods of time necessary to achieve a desired result. The desired result may be an improvement in the wound healing process (e.g., by reducing a surface area of the wound), remediation of the symptoms of the wound (e.g., pain, infection, and the like), shortening of the duration of any stage in the wound healing process, stabilization of the state of wound (e.g., infection), prevention or slowing of the development of wound progression, prevention of, delay or slowing of wound progression, delay or slowing of wound onset, amelioration or palliation of the wound state, and remission (whether partial or total), whether detectable or undetectable.

The term "topical administration" as used herein includes the contact of the wound compositions of the present invention with tissue on or about the wound area.

The term "parenteral administration" as used herein includes any form of administration in which a composition is delivered or absorbed into the patient without involving absorption via the intestines. Exemplary parenteral administrations that are used in the present invention include, but are not limited to intradermal or subcutaneous administration.

The term "treating" and "treatment" as used herein refers to an approach for obtaining beneficial or desired results, including clinical results. Beneficial or desired clinical results can include, but are not limited to, an improvement in the wound healing process (e.g., by reducing a surface area of the wound), remediation of the symptoms of the wound (e.g., pain, infection, and the like), shortening of the duration of any stage in the wound healing process or the overall wound healing process, stabilization of infection (if any), and remission (whether partial or total), whether detectable or undetectable.

Compounds and Compositions

The compounds described herein may be provided in any suitable form for administration to a wound of a patient. In one embodiment, the compounds are provided as pharmaceutical composition comprising a pharmaceutically acceptable carrier. In a typical embodiment, the compound is MCPIP or a variant or derivative thereof.

In one aspect, the pharmaceutically acceptable carrier may comprise a substrate, such as a natural or synthetic nonwoven or woven material, having the Compounds disposed on and/or therein to define a dressing that can be applied to, about, or adjacent to a wound. The substrate defining the dressing may be selected from the group consisting of a transdermal patch, a pad, a powder, a bandage, a host matrix, or any other suitable substrate configured to be applied to, over, and/or adjacent the wound. In certain embodiments, the dressing comprising the Compounds may be a hemostatic dressing as is known in the art. Exemplary hemostatic dressings are described in US Published Patent Application No. 20120282320, the entirety of which is hereby incorporated by reference. The Compounds may be impregnated within, otherwise dispersed within, and/or applied to a surface of the dressing using any suitable technique known in the art, such as by coating, spraying or dipping. It is appreciated that the dressing may include a polymeric coating or surface to be placed in contact with the wound, such as Teflon®, to avoid sticking of the dressing to the wound.

In addition, the wound compositions of the present invention may be provided and/or manufactured as a pharmaceutical composition for topical administration, parenteral administration, and/or any other suitable administration. It is understood that the active ingredient(s) and pharmaceutically acceptable carrier may be provided individually (with or without instructions for future mixing) or together (mixed, non-mixed, or with instructions for future mixing) in the respective formulation. Further, the wound composition may be prepared by known methods for the preparation of pharmaceutically acceptable compositions suitable for administration to a patient, such that an effective quantity of the active ingredients is combined in a mixture with a pharmaceutically acceptable carrier. Suitable pharmaceutically acceptable carriers are described, for example, in Remington's Pharmaceutical Sciences (Remington's Pharmaceutical Sciences, Mack Publishing Company, Easton, Pa., USA 1985).

In one embodiment, the wound composition is provided in the form of a topical composition that can be applied to, over, or adjacent the wound area. Without limitation, the topical composition may be in the form of a solution, a suspension, a spray, a cream, a gel, a foam, an ointment, a lotion, or a powder. The wound composition may be formulated as a controlled release, delayed release, or a sustained release formulation as is known in the art.

When a wound composition of the present invention is provided in the form of a topical composition, the wound composition may further include other cosmetic ingredients and pharmaceutically acceptable topical carriers which have substantially non-irritating, skin compatible components. Such suitable cosmetic and pharmaceutical agents include, but are not limited to, moisturizers, stabilizers, preservatives, antiseptics, lubricants, humectants, gelling agents, chelating agents, skin penetration enhancers, emollients, colorants, solvents, fatty bodies, thickening agents, emulsifiers, and/or any other excipient(s), which do not alter the therapeutic effect of the active ingredient(s) therein, e.g., Compounds.

In certain embodiments, the pharmaceutically acceptable carrier may include one or more of emulsifying agents, inert carriers including hydrocarbon bases, emulsifying bases, non-toxic solvents or water-soluble bases. Particularly suitable examples include pluronics, HPMC, CMC and other cellulose-based ingredients, lanolin, hard paraffin, liquid paraffin, soft yellow paraffin or soft white paraffin, white beeswax, yellow beeswax, cetostearyl alcohol, cetyl alcohol, dimethicones, emulsifying waxes, isopropyl myristate, microcrystalline wax, oleyl alcohol and stearyl alcohol.

Exemplary topical formulations to which the Nanoparticles may be included are set forth in U.S. Published Patent Application No. 20120289579, the entirety of which is hereby incorporated herein. It is appreciated that the active ingredient(s) described herein, e.g., Compounds, could replace or augment the active ingredient(s) described in U.S. Published Patent Application No. 20120289579.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

Typically a therapeutically effective dosage should produce a serum concentration of active compound of from about 0.1 ng/ml to about 50-100 μg/ml. The pharmaceutical compositions typically should provide a dosage of from about 0.001 mg to about 2000 mg of compound per kilo-gram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active compound may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Preferred pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. The concentration of active compound in the composition will depend on absorption, inactivation, excretion rates of the active compound, the dosage schedule, amount administered, particular formulation as well as other factors known to those of skill in the art.

Applications

The compositions and methods described herein may be utilized to promote the healing of any type of wound. The wound may include any disruption in the integrity of the skin or tissue as a result of: an external force (e.g., trauma); a disease or condition; aging; a burn resulting from exposure to sunlight, heat, and/or chemical reaction, for example; and/or as a result from damage by internal physiological processes. The wound may be open or closed. Further, the wound may be characterized as a non-healing wound, which includes but is not limited to incomplete healing wounds, and chronic wounds. Incomplete healing wounds have healed to a certain extent, but not to the extent expected for the time duration involved, or have not begun healing as expected for the time duration involved.

In certain embodiments, the wound is a chronic wound, which may be defined as a wound that has not healed within three months. Exemplary chronic wounds may include arterial ulcers, burn ulcers, decubitus ulcers, diabetic ulcers, diabetic foot ulcers, infectious ulcers, pressure ulcers, trauma-induced ulcers, ulcerations associated with pyoderma gangrenosum, venous ulcers, venous stasis ulcers, and vasculitic ulcers. It is appreciated that the wound may be associated with a particular disorder or condition, which renders the subject susceptible to, indirectly causes, or directly causes a non-healing wound. In certain embodiments, the subject is a diabetic, for example.

Kits

The compositions described herein may be provided in suitable packaging for maintaining the integrity of the article. In addition, the article may be provided as a kit along with suitable instructions that direct a user to use of a wound composition, e.g., pharmaceutical composition or dressing, comprising the Compounds in the treatment of a wound in a subject. The instructions may comprise user-readable and/or computer-readable information embodied on any suitable medium, such as a paper insert or a computer-readable disc. Alternatively, the instructions may direct the user to an external source, such as to a website, where such instructions may be found.

Dosing

One skilled in the art would readily appreciate that the administration, duration, and dosing of the wound compositions may be determined or adjusted based on the age, body weight, general condition, sex, diet, the severity of the wound, and/or degree of inflammation and/or infection associated with the wound. Effective amounts of the wound composition can be given repeatedly, depending upon the effect of the initial treatment regimen. Administrations are typically given periodically, while monitoring any response. It will be recognized by a skilled person that lower or higher dosages or number of applications other than those indicated herein may be given, according to the administration schedules and routes selected. In certain embodiments, the compounds may be provided in a composition, such as a topical composition or an injectable composition, in a concentration of at least 1 μM, and in particular embodiments, at least 10 μM.

In an embodiment, the wound compositions may be administered at least once daily for at least a first week's time. Thereafter, the wound compositions may be applied to the wound at greater intervals, such as once a week, until such time as the wound is satisfactorily healed. In one embodiment, a wound composition is applied once a week (after the initial daily application) for a period of at least seven weeks. It is understood that prior to each application, the wound may be rinsed with a sterile solution, such as saline, and allowed to dry. Thereafter, a wound composition may be applied.

Conjunctive Agents

In accordance with another aspect, the wound compositions comprising Compounds described herein may be employed alone in the treatment, or may be combined with a conjunctive agent, which is administered to the patient independently of the wound composition or as part of the same formulation. Such conjunctive agents may be delivered simultaneously, before and/or after the administration of the wound composition. Suitable conjunctive agents may include, by way of example only, vasodilators, vasoconstrictors, hypertensive agents, antibacterial agents, antibiotics, antioxidants, antifungal agents, non-steroidal antiinflammatory agents, steroidal agents, anesthetics, and/or diabetes agents.

Suitable vasodilators include, but are not limited to, manidipine, nicardipine, nilvadipine, nisoldipine, nitrendipine, benidipine, amlodipine, aranidipine, budralazine, cadralazine, ecarazine, hydralazine, todralazine, oxyphedrine, diltiazem, tolazoline, hexobendine, bamethan, clonidine, methyldopa, guanabenz, and the like.

Suitable vasoconstrictors include, but are not limited to, dopamine, dobutamine denopamine and the like.

Suitable hypertensive agents include, but are not limited to, dopamine, dobutamine, denopamine, digitoxin, digoxin, methyldigoxin, lanatoside C, G-strophantin, and the like.

Suitable antibacterial agents include, but are not limited to, sulfonamides, such as sulfamethizole, sulfisoxazole, sulfamonomethoxin, sulfamethizole, salazosulfapyridine, silver sulfadiazine, and the like, and quinolones, such as nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin, and the like.

Suitable antibiotics include, but are not limited to, tetracyclin hydrochloride, ampicillin, piperacillin, gentamycin, dibekacin, kanendomycin, lividomycin, tobramycin, amikacin, fradiomycin, sisomicin, tetracyclin, oxytetracyclin, rolitetracyclin, doxycyclin, ampicillin, piperacillin, ticarcillin, cefalotin, cefapirin, cefaloridine, cefaclor, cefalexin, cefroxadine, cefadroxil, cefamandole, cefotoam, cefroxime, cefotiam, cefotiam hexetil, cefuroxime axetil, cefdinir, cefditoren pivoxil, ceftazidime, cefpiramide, cefsulodin, cefinenoxime, cefpodoxime proxetil, cefpirome, cefozopran, cefepime, cefsulodin, cefinenoxime, cefinetazole, cefminox, cefoxitin, cefbuperazone, latamoxef, flomoxef, cefazolin, cefotaxime, cefoperazon, ceftizoxime, moxalactam, thienamycin, sulfazecin, azthreonam and their salts, griseofulvin, lankacidin [J. Antibiotics, 38, 877-885 (1985)], and the like.

Suitable antioxidants may include, but are not limited to, superoxide dismutase Vitamin C (Ascorbic Acid), Vitamin D, Vitamin E, α-lipoic Acid, metronidazole, elemental antioxidants, β-glucan, curcumin, epigallocatechin gallate, proanthocyanidins, propolis, honey, and the like.

Suitable antifungal agents include, but are not limited to, polyene-based antibiotics (e.g., amphotericin B, nystatin, trichomycin); griseofulvin, pyrrolnitrin, and the like; cytosine metabolism antagonists (e.g., flucytosine); imidazole derivatives (e.g., econazole, clotrimazole, miconazole nitrate, bifonazole, croconazole); triazole derivatives (e.g., fluconazole, itraconazole, azole-based compounds, e.g., [2-[(1R, 2R)-2-(2,4-difluorophenyl)-2-hydroxy-1-methyl-3-(1H-1,2, 4-t-riazol-1-yl)propyl]-4-[4-(2,2,3,3-tetrafluoropropoxy) phenyl-3-(2H,4H)-1,2,-4-triazolone); thiocarbamic acid derivatives (e.g., trinaphthol); echinocandin-based derivatives (e.g., caspofamgine, FK-463, V-Echinocadin), and the like.

Suitable non-steroidal antiinflammatory agents include, but are not limited to, acetaminophen, fenasetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizol, tiaramide hydrochloride, zaltoprofen, gabexate mesilate, camostat mesilate, ulinastatin, colchicine, probenecid, sulfinpyrazone, benzbromarone, allopurinol, sodium gold thiomalate, sodium hyaluronate, sodium salicylate, morphine hydrochloride, salicylic acid, atropine, scopolamine, morphine, pethidine, levorphanol, ketoprofen, naproxen, oxymorphone, and their salts.

Suitable steroidal agents include, but are not limited to, dexamethasone, hexestrol, methimazole, betamethasone, triamcinolone, triamcinolone acetonide, fluorocinonide, fluorocinolone acetonide, prednisolone, methylprednisolone, cortisone acetate, hydrocortisone, fluorometholone, beclometasone dipropionate, estriol, and the like.

Suitable anesthetics include, but are not limited to, cocaine hydrochloride, procaine hydrochlodie, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine, and the like, or other systemic, inhalation, or intravenous anesthetics.

Suitable diabetes agents include, but are not limited to, actos, lodiglitazon, kinedak, penfill, humalin, euglucon, glimicron, daonil, novolin, monotard, insulins, glucobay, dimelin, rastinon, bacilcon, deamelin S, Iszilins]; hypothyroidism treating agent [dried thyroid gland (thyreoid), levothyroxine sodium (thyradin S), liothyronidin sodium (thyronine, thyromin), and the like.

The ratio between a compound of the present invention and a conjunctive agent in a concomitant formulation may be selected appropriately on the basis of the target, route, and disease/condition of the patient and may be readily determined by one skilled in the art. In a particular embodiment, the present invention includes a method of treating a wound comprising administering to a patient in need thereof a wound composition comprising an effective amount of Compounds with an effective amount of an antibiotic to aid in combating wound infection.

Alternative Modes of Administration

The compounds for use in the method of the invention are typically formulated for topical or local administration but can also be formulated for oral, transdermal, sublingual, buccal, parenteral, rectal, intranasal, intraocular, intrabronchial or intrapulmonary administration. For oral administration the compounds can be of the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets can be coated using suitable methods and coating materials such as OPADRY film coating systems available from Colorcon, West Point, Pa. (e.g., OPADRY, OY Type, OY-C Type, Organic Enteric OY-P Type, Aqueous Enteric OY-A Type, OY-PM Type and OPADRY® White, 32K18400).

In a particular embodiment, the oral form is a tablet containing MCPIP and a pharmaceutically acceptable excipient, such as, but not limited to, mannitol, corn starch, microcrystalline cellulose, colloidal silicon dioxide, polyvinyl pyrrolidone, talc, magnesium stearate, and the like which are optionally coated with an OPADRY film coating.

Liquid preparation for oral administration can be in the form of solutions, syrups or suspensions. The liquid preparations can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

For buccal administration, the compounds for use in the method of the invention can be in the form of tablets or lozenges formulated in a conventional manner.

For parenteral administration, the compounds for use in the method of the invention can be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents can be used.

For rectal administration, the compounds for use in the method of the invention can be in the form of suppositories or enemas.

For sublingual administration, tablets can be formulated in conventional manner.

For intranasal, intraocular, intrabronchial or intrapulmonary administration, conventional formulations can be employed.

Further, the compounds (e.g. protein or delivery vehicle) for use in the method of the invention can be formulated in a sustained release preparation. For example, the compounds can be formulated with a suitable polymer or hydrophobic material which provides sustained and/or controlled release properties to the active agent compound. As such, the compounds for use the method of the invention can be administered in the form of microparticles for example, by injection or in the form of wafers or discs by implantation.

Delivery Vehicles

1) Viral Vectors

In accordance with the method of the invention, an expression vector is a viral or a non-viral expression vector. Viral expression vectors which may be used advantageously in the method of the invention include, but are not limited to, an adeno associated virus (AAV) vector, a lentivirus vector, an adenovirus vector, and a herpes simplex virus (HSV) vector.

In a preferred embodiment, the compositions of the invention can be tailored to include a nucleic acid sequence (e.g., SEQ ID NO: 1, derivatives, fragments and variants thereof) in an expression vector. Viral vectors for use in the invention are those that exhibit low toxicity to a host cell. Viral vector methods and protocols that may be used in the invention are reviewed in Kay et al. Nature Medicine 7:33-40, 2001. The use of specific vectors, including those based on adenoviruses, adeno-associated viruses, herpes viruses, and retroviruses are described in more detail below.

The use of recombinant adenoviruses as vectors is discussed in W. C. Russell, Journal of General Virology 81:2573-2604, 2000; and Bramson et al., Curr. Opin. Biotechnol. 6:590-595, 1995. Adenovirus vectors are preferred for use in the invention because they (1) are capable of highly efficient gene expression in target cells and (2) can accommodate a relatively large amount of heterologous (non-viral) DNA. A preferred form of recombinant adenovirus is a "gutless", "high-capacity", or "helper-dependent" adenovirus vector. Such a vector features, for example, (1) the deletion of all or most viral-coding sequences (those sequences encoding viral proteins), (2) the viral inverted terminal repeats (ITRs) which are sequences required for viral DNA replication, (3) up to 28-32 kb of "exogenous" or "heterologous" sequences (e.g., sequences encoding an ammonia producing enzyme), and (4) the viral DNA packaging sequence which is required for packaging of the viral genomes into infectious capsids. For specifically targeting liver, preferred variants of such recombinant adenoviral vectors contain tissue-specific enhancers and promoters operably linked to for example, SEQ ID NO: 1.

Other viral vectors that might be used in the invention are adeno-associated virus (AAV)-based vectors. AAV-based vectors are advantageous because they exhibit high transduction efficiency of target cells and can integrate into the host genome in a site-specific manner. Use of recombinant AAV vectors is discussed in detail in Tal, J., J. Biomed. Sci. 7:279-291, 2000 and Monahan and Samulski, Gene Therapy 7:24-30, 2000. A preferred AAV vector comprises a pair of AAV inverted terminal repeats which flank at least one cassette containing a tissue (e.g., gum)- or cell-specific promoter operably linked to a urease nucleic acid. The DNA sequence of the AAV vector, including the ITRs, the promoter and, for example, urease gene may be integrated into the host genome.

The use of herpes simplex virus (HSV)-based vectors is discussed in detail in Cotter and Robertson, Curr. Opin. Mol. Ther. 1:633-644, 1999. HSV vectors deleted of one or more immediate early genes (IE) are advantageous because they are generally non-cytotoxic, persist in a state similar to latency in the host cell, and afford efficient host cell transduction. Recombinant HSV vectors can incorporate approximately 30 kb of heterologous nucleic acid. A preferred HSV vector is one that: (1) is engineered from HSV type I, (2) has its IE genes deleted, and (3) contains a tissue-specific promoter operably linked to a urease nucleic acid. HSV amplicon vectors may also be useful in various methods of the invention. Typically, HSV amplicon vectors are approximately 15 kb in length, and possess a viral origin of replication and packaging sequences.

Retroviruses such as C-type retroviruses and lentiviruses might also be used in the invention. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells. They are also highly efficient at transducing human epithelial cells. Lentiviral vectors for use in the invention may be derived from human and non-human (including SIV) lentiviruses. Preferred lentiviral vectors include nucleic acid sequences required for vector propagation as well as a tissue-specific promoter operably linked to, for example, SEQ ID NO: 1, derivatives, variants and fragments thereof. These former may include the viral LTRs, a primer binding site, a polypurine tract, att sites, and an encapsidation site.

A lentiviral vector may be packaged into any suitable lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN), might also be used in the invention. Use of alphaviruses is described in Lundstrom, K., Intervirology 43:247-257, 2000 and Perri et al., Journal of Virology 74:9802-9807, 2000. Alphavirus vectors typically are constructed in a format known as a replicon. A replicon may contain (1) alphavirus genetic elements required for RNA replication, and (2) a heterologous nucleic acid such as one encoding SEQ ID NO: 1. Within an alphavirus replicon, the heterologous nucleic acid may be operably linked to a tissue-specific promoter or enhancer.

Recombinant, replication-defective alphavirus vectors are advantageous because they are capable of high-level heterologous (therapeutic) gene expression, and can infect a wide host cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a host cell. The replicons may also exhibit transient heterologous nucleic acid expression in the host cell. A preferred alphavirus vector or replicon is non-cytopathic.

In many of the viral vectors compatible with methods of the invention, more than one promoter can be included in the vector to allow more than one heterologous gene to be expressed by the vector. Further, the vector can comprise a sequence which encodes a signal peptide or other moiety which facilitates the secretion of a gene product from the host cell.

To combine advantageous properties of two viral vector systems, hybrid viral vectors may be used to deliver a nucleic acid to a target tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral lilts may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the host cell genome and effect stable urease gene expression.

Other nucleotide sequence elements which facilitate expression of SEQ ID NO: 1, derivatives, variants and fragments thereof and cloning of the vector are further contemplated. For example, the presence of enhancers upstream of the promoter or terminators downstream of the coding region, for example, can facilitate expression.

In an aspect of the method wherein the viral expression vector is an AAV vector capable of transducing the target cell, the AAV vector is free of both wildtype and helper virus. Exemplary types of AAV vectors useful in the present invention include serotype 2 AAV vectors and chimeric serotype ½ AAV vectors.

2) Other Delivery Vehicles

Many nonviral techniques for the delivery of a nucleic acid sequence into a cell can be used, including direct naked DNA uptake (e.g., Wolff et al., Science 247: 1465-1468, 1990), receptor-mediated DNA uptake, e.g., using DNA coupled to asialoorosomucoid which is taken up by the asialoglycoprotein receptor in the liver (Wu and Wu, J. Biol. Chem. 262: 4429-4432, 1987; Wu et al., J. Biol. Chem. 266: 14338-14342, 1991), and liposome-mediated delivery (e.g., Kaneda et al., Expt. Cell Res. 173: 56-69, 1987; Kaneda et al., Science 243: 375-378, 1989; Zhu et al., Science 261: 209-211, 1993). Many of these physical methods can be combined with one another and with viral techniques; enhancement of receptor-mediated DNA uptake can be effected, for example, by combining its use with adenovirus (Curiel et al., Proc. Natl. Acad. Sci. USA 88: 8850-8854, 1991; Cristiano et al., Proc. Natl. Acad. Sci. USA 90: 2122-2126, 1993). Other examples include stem cells such as mesenchymal stem cells, hematopoietic stem cells, cardiac stem cells or neural stem cells, embryonic stem cells that have been engineered to express MCPIP. Such stem cells can be administered in such a way to be incorporated in to tissues of a patient in need. In a particular embodiment, stem cells are administered to myocardial tissue. Bu L, et al "Human ISL1 heart progenitors generate diverse multipotent cardiovascular cell lineages" Nature 2009 460:113-117.

Polynucleotides and Polypeptides

Aspects of the invention therefore include polynucleotides encoding at least one mammalian MCPIP and amino acid sequences representing at least one MCPIP protein. Aspects of the invention also include subunits or variants of polynucleotides or MCPIP proteins or peptides encoded by those polynucleotides. The terms "protein" and "polypeptide" are used interchangeably herein, unless specified otherwise.

It is well known in the art that a single amino acid may be encoded by more than one nucleotide codon—and that the nucleotide sequence may be easily modified to produce an alternate nucleotide sequence that encodes the same peptide. Therefore, alternate embodiments of the present invention include alternate DNA sequences encoding peptides containing the amino acid sequences described for MCPIP. DNA sequences encoding peptides containing the claimed amino acid sequence include DNA sequences which encode any combination of the claimed sequence and any other amino acids located N-terminal or C-terminal to the claimed amino acid sequence.

It is to be understood that amino acid and nucleic acid sequences may include additional residues, particularly N- or C-terminal amino acids or 5' or 3' nucleotide sequences, and still be essentially as set forth in the sequences disclosed herein, as long as the sequence produces a functionally similar polypeptide or protein. A nucleic acid fragment of almost any length may be employed, and may be combined with other DNA sequences, such as promoters, polyadenylation signals, additional restriction enzyme sites, multiple cloning sites, other coding segments, and the like. Therefore, overall length may vary considerably.

MCPIP polypeptides, as used herein, may comprise short fragments of proteins often referred to as peptides, as well as longer fragments generally referred to as polypeptides, and full-length proteins. These polypeptides can be prepared by standard peptide synthesis methods known to those of skill in the art, but may also be produced using an expression vector having a polynucleotide sequence encoding the polypeptide (s) of choice operably linked to appropriate promoter, terminator, and other functional sequences (such as a sequence encoding a purification tag) to facilitate expression and purification of the peptides.

It is to be understood that amino acid and nucleic acid sequences may include additional residues, particularly N- or C-terminal amino acids or 5' or 3' nucleotide sequences, and still be essentially as set forth in the sequences disclosed herein, as long as the sequence confers MCP-1 inducible transcription factor activity upon the polypeptide or protein moiety of the expressed protein. Nucleic acids which hybridize with a nucleic acid encoding the amino acid sequence of SEQ ID NO: 2 or SEQ ID NO: 4 under stringent conditions and encode a polypeptide having a similar MCP-1 inducible transcription factor activity to that of a polypeptide comprising SEQ ID NO: 2 or SEQ ID NO: 4 are also included as embodiments of the present invention.

The term "moderately stringent conditions", as used herein, means conditions in which non-specific hybridization will not generally occur. Hybridization under such conditions can be performed based on the description provided in Molecular Cloning: A Laboratory Manual 2nd ed., published by cold Spring Harbor Laboratory in 1989, edited by T. Maniatis et al. Typically, for stringent hybridization conditions a combination of temperature and salt concentration should be chosen that is approximately 12-20° C. below the calculated $T_m$ of the hybrid under study. The $T_m$ of a hybrid between a polynucleotide of interest or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m=81.5°\,C.-16.6(\log_{10}[Na^+])+0.41(\%G+C)-0.63\,(\%\text{formamide})-600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C. According to another example, stringent conditions include incubation with a probe in 6×SSC containing 0.5% SDS, 5×Denhardt's solution and 100 micrograms/ml salmon sperm DNA at 60 degrees C.

Additional nucleic acid bases may be added either 5' or 3' to the MCPIP ORF, and may be combined with other DNA sequences, such as promoters, polyadenylation signals, additional restriction enzyme sites, multiple cloning sites, other coding segments, and the like. Therefore, overall length of such a polynucleotide may vary considerably. In a method described by the present invention, a nucleotide sequence of SEQ ID NO: 1 is inserted into a protein expression vector to produce a protein which can be used to synthesize a DNA copy of an RNA molecule. The DNA can then be amplified to form multiple copies.

"Control sequences" are those DNA sequences that are necessary for the expression of a protein from a polynucleotide sequence containing such a sequence, operably linked to the polynucleotide sequence encoding the protein. These sequences include prokaryotic sequences such as, for example, promoters, operators, and ribosome binding sites, and eukaryotic sequences such as, for example, promoters, enhancers, and polyadenylation signals. "Expression systems" are DNA sequences (such as, for example, plasmids) appropriate for expression of a target protein in a particular host cell, these sequences comprising appropriate control sequences for protein expression in the host cell operably linked to the polynucleotide sequence encoding the target protein.

It is to be understood that a "variant" of a polypeptide is not completely identical to the native protein. A variant MCPIP protein, for example, can be obtained by altering the amino acid sequence by insertion, deletion or substitution of one or more amino acids. The amino acid sequence of the protein can be modified, for example, by substitution to create a polypeptide having substantially the same or improved qualities as compared to the native polypeptide. The substitution may be a conserved substitution. A "conserved substitution" is a substitution of an amino acid with another amino acid having a side chain that is similar in polar/nonpolar nature, charge, or size. The 20 essential amino acids can be grouped as those having nonpolar side chains (alanine, valine, leucine, isoleucine, proline, phenylalanine, and tryptophan), uncharged polar side chains (methionine, glycine, serine, threonine, cystine, tyrosine, asparagine and glutamine), acidic side chains (aspartate and glutamate), and basic side chains (lysine, arginine, and histidine). Conserved substitutions might include, for example, Asp to Glu, Asn, or Gln; His to Lys, Arg or Phe; Asn to Gln, Asp or Glu; and Ser to Cys, Thr or Gly. Alanine, for example, is often used to make conserved substitutions.

To those of skill in the art, variant polypeptides can be obtained by substituting a first amino acid for a second amino acid at one or more positions in the polypeptide structure in order to affect biological activity. Amino acid substitutions may, for example, induce conformational changes in a polypeptide that result in increased biological activity.

Those of skill in the art may also make substitutions in the amino acid sequence based on the hydrophilicity index or hydropathic index of the amino acids. A variant amino acid molecule of the present invention, therefore, has less than one hundred percent, but at least about fifty percent, and preferably at least about eighty to about ninety percent amino acid sequence homology or identity to the amino acid sequence of a polypeptide comprising SEQ ID NO: 2, or a polypeptide encoded by SEQ ID NO: 4. Therefore, the amino acid sequence of the variant MCPIP protein corresponds essentially to the native MCPIP protein amino acid sequence. As used herein, "corresponds essentially to" refers to a polypeptide sequence that will elicit a similar biological and enzymatic activity to that generated by a MCPIP protein comprising SEQ ID NO 2 or SEQ ID NO: 4, such activity being at least about 70 percent that of the native MCPIP protein, and more preferably greater than 90 percent of the activity of the native MCPIP protein.

A variant of the MCPIP protein may include amino acid residues not present in a corresponding MCPIP protein comprising SEQ ID NO 2, or may include deletions relative to the MCPIP protein comprising SEQ ID NO 2. A variant may also be a truncated "fragment," as compared to the corresponding protein comprising SEQ ID NO 2, the fragment being only a portion of the full-length protein.

Polypeptides of the invention may be delivered to a cell via attachment of one or more polypeptides to cell permeable, or "importation competent" signal peptide sequences, and membrane translocation sequences that have been shown to facilitate the transport of attached peptides and proteins into cells. Several sequences of this kind have previously been described, including the hydrophobic region of the signal sequence of Kaposi fibroblast growth factor which has been fused to the nuclear localization sequence (NLS) of p50 to produce the peptide known as SN50 (U.S. Pat. No. 5,807,746, Lin et al.). Polypeptides may also be delivered via a membrane translocating sequence described in U.S. Pat. Nos. 6,248,558; 6,432,680; and 6,780,843 (Rojas et al.). MCPIP, or a nuclear localization sequence that blocks nuclear localization of MCPIP, may also be delivered via the cell-permeable sequence described in U.S. Patent Application Number 20060099275 (Lin and Budu). Other membrane-translocating sequences are also well-known to those of skill in the art. Non-invasive delivery of proteins via membrane translocating peptides is discussed by Hawiger in Curr. Opin Chem. (1999) 3: 89-94, and multiple examples of both in vitro and in vivo use of membrane translocation via cell-permeable peptide sequences are available in the literature. The HIV-Tat peptide, for example, has been used in a number of studies to deliver cargo peptides to target cells (Ribeiro, M. M., et al. Biochem. Biophys. Res. Commun. (2003) 305(4): 876-81; Jung, H. J., et al. Biochem. Biophys. Res. Commun. (2006) 345(1): 222-228; Barnett, E. M., et al. Invest. Ophthalmol. Vis. Sci. (2006) 47(6): 2589-2595; Hoque, M., et al. J. Biol. Chem. (2005) 280(14): 13648-13657; Mondal D., et al. Exp. Biol. Med. (2005) 230(9): 631-644; Kittiworakam, J., et al. J. Biol. Chem. (2006) 281(6): 3105-3115).

Polynucleotides encoding all or a part of the amino acid sequence of MCPIP may be delivered in vitro or in vivo by a variety of means known to those of skill in the art, such as, for example, viral gene delivery, naked DNA, delivery via cationic lipid carriers, and plasmid DNA/polylysine complexes.

As used herein, MCPIP polypeptides include variants or biologically active fragments of the peptides, as well as peptides which may contain additional amino acids either N-terminal or C-terminal (or both) to the disclosed sequences, their derivatives, variants, or functional counterparts. A "functional counterpart" can include, for example, a peptide nucleic acid (PNA). A "variant" of the peptide is not completely identical to a disclosed MCPIP polypeptide sequence. A variant, given the disclosure of the present invention, can be obtained by altering the amino acid sequence by insertion, deletion or substitution of one or more amino acid. The amino acid sequence of a disclosed peptide can be modified, for example, by substitution to create a peptide having substantially the same or improved qualities. The substitution may be a conserved substitution. A "conserved substitution" is a substitution of an amino acid with another amino acid having a side chain that is similar in polar/nonpolar nature, charge, or size. The 20 essential amino acids can be grouped as those having nonpolar side chains (alanine, valine, leucine, isoleucine, proline, phenylalanine, and tryptophan), uncharged polar side chains (methionine; glycine, serine, threonine, cysteine, tyrosine, asparagine and glutamine), acidic side chains (aspartate and glutamate) and basic side chains (lysine, arginine, and histidine). Conserved substitutions might include, for example, Asp to Glu, Asn or Gln; His to Lys, Arg or Phe; Asn to Gln, Asp or Glu, Leu to Ile or Val, and Ser to Cys, Thr or Gly. Alanine is commonly used to make conserved substitutions.

To those of skill in the art, variant polypeptides can be obtained by substituting a first amino acid for a second amino acid at one or more positions in the peptide structure in order to affect biological activity. Amino acid substitutions may, for example, induce conformational changes in a polypeptide that result in increased biological activity. Those of skill in the art may also make substitutions in the amino acid sequence based on the hydrophilicity index or hydropathic index of the amino acids.

A variant polypeptide of the present invention has less than 100%, but at least about 50%, and more preferably at least about 80% to about 90% amino acid sequence homology or identity to the amino acid sequence of a corresponding native nucleic acid molecule or polypeptide comprising SEQ ID NO 1, SEQ ID NO 2, SEQ ID NO 3, or SEQ ID NO 4. The amino acid sequence of a variant MCPIP polypeptide therefore corresponds essentially to the disclosed amino acid sequences. As used herein, "corresponds essentially to" refers to a polypeptide sequence that will elicit a similar biological activity as that generated by a disclosed MCPIP, such activity being from at least about 70 percent of that of disclosed MCPIP polypeptide, to greater than 100 percent of the activity of a disclosed MCPIP peptide.

The human MCPIP polypeptide sequence comprises a Zc3h12a Ribonuclease domain at residues 130-280 and zinc finger domain at 284-309. It is to be understood that non-conserved substitutions at these regions will likely result in negating activity of the protein. Mizgalska et al., FEBS Journal 276:7386-7399 (2009). Conserved substitutions in these domains will likely result in preserving activity of the protein. Most mutations, whether conservative or non-conservative, outside the two domains will not likely affect activity of the protein to any great extent. Accordingly, the disclosure of SEQ ID NO: 2 combined with the knowledge in the art regarding the genetic code establishes possession of using the genus of nucleic acid sequences that encode SEQ ID NO. 2, as well as sequences that encode a polypeptide with at least 85 percent sequence identity with SEQ ID NO. 2.

A variant of a disclosed MCPIP may include amino acid residues not present in the corresponding MCPIP, or may include deletions relative to the corresponding MCPIP. A variant may also be a truncated "fragment" as compared to the corresponding MCPIP, i.e., only a portion of the amino acid sequence of certain disclosed MCPIPs. The fragment may be at least 20, 30, 40, 50, 60, 80, 90, 100, 150, 175, 200, 250, 300, 350, 400, 450, 500, 550, 560, 570, 580, 585, 590, or 595 amino acids in length.

Variants, including fragments, possessing activity of MCPIP, refer to those, that are capable of degrading interleukin 1-beta (see Mizgalska et al.). Alternatively, the variant has activity according to the in vitro assay for transcription factor activity as taught in Zhou et al., Circulation Research, 98:1177-1185 (2006). Preferably, naturally or non-naturally occurring polypeptide variants have amino acid sequences which are at least about 55, 60, 65, or 70, preferably about 75, 80, 85, 90, 96, 96, or 98% identical to the full-length amino acid sequence or a fragment thereof. Percent identity between a putative polypeptide variant and a full length amino acid sequence is determined using the Blast2 alignment program (Blosum62, Expect 10, standard genetic codes).

EXAMPLES

Example 1

Expression of MCPIP on Scratch-Induced Wound Healing in HaCaT Cells

Cells were cultured to confluence and transfected with GFP or MCPIP vectors for 48 hrs and wounded by scratching. Cells were then incubated for the indicated hours and photographed. See FIG. 1A. The scratch induced wound healing during 24 hrs after scratching was then quantified. The wound distance was quantified and it was shown enhanced expression of MCPIP caused a significant decrease in wound distance. This was correlated with HaCAt cell migration. see FIG. 1B.

Example 2

Knockdown of MCPIP Inhibited Migration of HaCaT Cells

Figure 2:
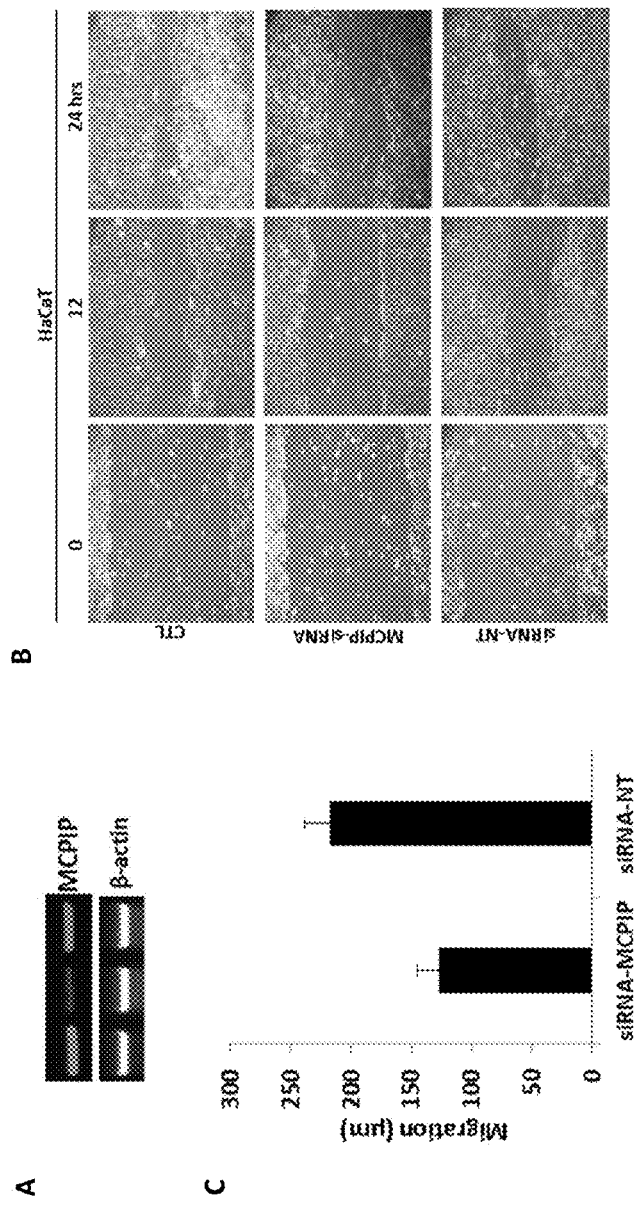
FIG. 2. Knockdown of MCPIP inhibited migration of HaCaT cells. (A) HaCaT cells were cultured and transfected with MCPIP siRNA or non-targeted siRNA for 48 hrs, RT-PCR was performed to confirm that siRNA efficiently knockdown of MCPIP mRNA levels. (B) Cells were cultures to confluence and wounded by scratching. Cells were then incubated for the indicated hours and photographed. (C) Quantification of cell migration during 24 h after scratching.

HaCaT cells were cultured and transfected with MCPIP siRNA or non-targeted siRNA for 48 hrs. RT-PCR was performed to confirm that siRNA efficiently knockdown of MCPIP mRNA levels. FIG. 2A is a photograph of a gel of RT-PCR samples showing that MCPIP siRNA efficiently knocks down MCPIP. HaCaT Cells were cultured to confluence and wounded by scratching. Cells were then incubated for 0, 12, and 24 hours and then photographed (FIG. 2b). Migration of the cells proximate to the scratch wound was measured at 24 hours. FIG. 2C shows that HaCaT cells transfected with MCPIP siRNA show a significant decrease in migration.

Example 3

Figure 3:
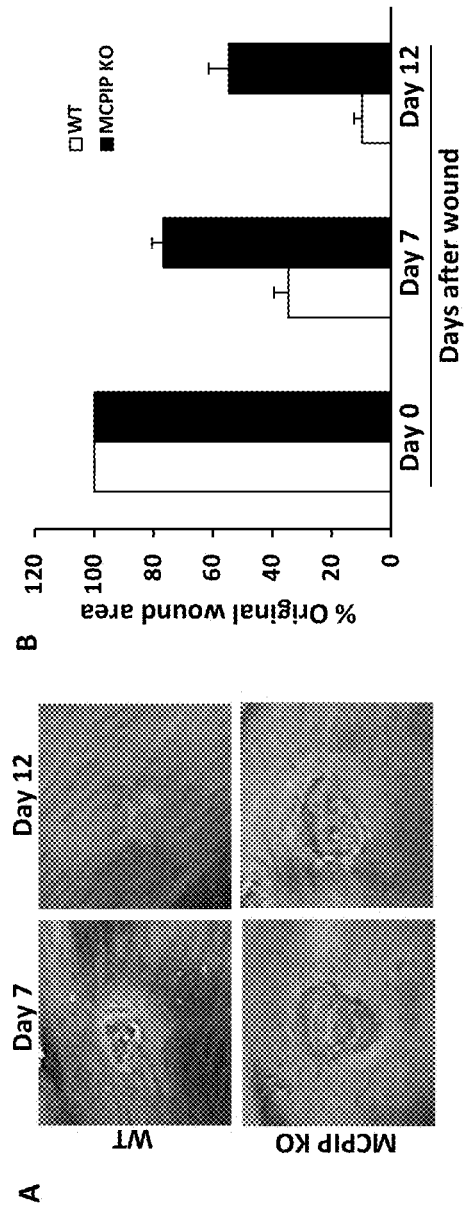
FIG. 3. Lack of MCPIP impaired wound healing in MCPIP KO mice. (A) Wound sites were photographed at the indicated time. (B) Changes in percentage of wound area at each time point compared with the original wound area.

Lack of MCPIP Impaired Wound Healing in MCPIP KO Mice (A) Wounds were formed on the epidermis of MCPIP KO mice and wild type mic. Wound sites were photographed at day 7 and day 12. FIG. 3A clearly shows that the level of wound healing in the MCPIP knockout mice is significantly less in as compared to wild-type. Changes in percentage of wound area at the day 7 and day 12 time points of the knockout and wild-type mice were compared with the original wound area. The percentage of the wound area at day 7 and 12 is dramatically greater in the knockout mice as compared to wild-type (FIG. 3C).

Example 4

Expression of MCPIP Enhanced Wound Healing in Diabetic Mice

Induction of MCPIP was found in the wound skin but not in the healed skin (see FIG. 4). As shown in FIG. 4(B), wound sites were photographed at day 0, 3, 7 and 12. Day 0 pictures were taken immediately after the wound. Changes in percentage of wound area at each time point compared with the original wound area, which is shown in FIG. 4C. The level of healing in the MCPIP enhanced animals is clearly greater than the control. FIG. 4D shows the expression of cytokines in wound skins at day 12 after wound. Expression of PECAM and VEFF in wound skins at day 12 was examined by RT-PCR (see FIG. 4F).

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); *Arabidopsis*, Meyerowitz et al, Eds., Cold Spring Harbor Laboratory Press, New York (1994) and the various references cited therein.

Finally, while various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference in their entirety to the extent they are not inconsistent with the teachings herein.

What is claimed is:

1. A topical composition for application to a wound in a subject to promote healing of the wound, the wound composition comprising:
   an effective amount of MCPIP polypeptide for treatment of the wound; and
   a pharmaceutically acceptable carrier in a form configured for topical administration to the subject.

2. The topical composition of claim 1, which is in a form selected from the group consisting of a solution, a suspension, a spray, a cream, a gel, a foam, an ointment, a lotion, and a powder.

3. The topical composition of claim 1, wherein the pharmaceutically acceptable carrier comprises a dressing, the dressing selected from the group consisting of a transdermal patch, a pad, a powder, a matrix, and a bandage.

4. A kit comprising:
   a pharmaceutical composition comprising an effective amount of MCPIP for treating a wound and a pharmaceutically acceptable carrier; and
   instructions directing a user to use of the pharmaceutical composition in the treatment of a wound in a subject.

5. The kit of claim 4, wherein the wound is at least one of a wound selected from the group consisting of an incomplete healing wound, a chronic wound, a burn, and a wound caused by trauma.

6. The kit of claim 4, wherein the pharmaceutical composition is in a form from the group consisting of a solution, a suspension, a spray, a cream, a gel, a foam, an ointment, a lotion, or a powder.

7. The kit of claim 4, wherein the pharmaceutically acceptable carrier comprises a dressing, the dressing selected from the group consisting of a transdermal patch, a pad, a powder, a matrix, and a bandage.

\* \* \* \* \*